United States Patent [19]

Cragoe, Jr. et al.

[11] 4,115,402

[45] Sep. 19, 1978

[54] 2,3-DICHLORO-4-[(SUBSTITUTED-SULFONYL)-PHENOXY]-ACETIC ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 807,478

[22] Filed: Jun. 17, 1977

[51] Int. Cl.$^2$ .................... C07D 333/24; A01N 9/00
[52] U.S. Cl. .................... 260/332.2 A; 260/347.2; 424/275; 424/285; 424/353; 562/429
[58] Field of Search .................... 260/332.2 A

[56] References Cited

U.S. PATENT DOCUMENTS

| 3,682,968 | 8/1972 | Shen | 260/332.2 A |
| 3,758,506 | 9/1973 | Godfroid | 260/332.2 A |

*Primary Examiner*—A. Siegel
*Attorney, Agent, or Firm*—Michael C. Sudol, Jr.

[57] ABSTRACT

2,3-Dichloro-4-[(substituted sulfonyl)phenoxyl]-acetic acids and their salt, ester and amide derivatives thereof. The products are useful diuretic, saluretic and uricosuric agents. The acid products are prepared by treating a 2,3-dichloro-4-(2-substituted sulfonyl)phenol with a haloalkanoic acid or ester thereof and if the ester is employed hydrolyzing the ester.

4 Claims, No Drawings

2,3-DICHLORO-4-[(SUBSTITUTED-SULFONYL)-PHENOXY]-ACETIC ACIDS

SUMMARY AND BACKGROUND OF THE INVENTION

The invention relates to a new class of chemical compounds which can be described generally as 2,3-dichloro4-[(substituted sulfonyl)phenoxy]acetic acids and to the non-toxic pharmacologically acceptable salts and esters thereof.

It is also an object of this invention to describe a method for the preparation of these compounds. Pharmacological studies show that the instant products are effective diuretic and saluretic agents which can be used in the treatment of conditions associated with electrolyte and fluid retention. The instant products are also useful in the treatment of hypertension. In addition, these compounds are able to maintain the uric acid concentration in the body at pretreatment levels or to even effect a decrease in the uric acid concentration. All of the compounds of this invention possess the described utilities; however, by structural modifications various ratios of these biological activities are observed.

When administered in therapeutic dosages, in conventional vehicles, the instant products effectively reduce the amount of sodium and chloride ions in the body, lower dangerous excesses of fluid levels to acceptable levels and, in general, alleviate conditions usually associated with edema. In addition, these compounds overcome a major problem associated with many of the presently available diuretics and saluretics. Many of the presently available diuretics and saluretics have a tendency upon administration to induce hyperuricemia which may precipitate uric acid or sodium urate, or both, in the body which may cause from mild to severe cases of gout. The instant compounds of this invention now provide an effective tool to treat those patients (both human and animal) requiring diuretic and saluretic treatment without incurring the risk of inducing gout.

The 2,3-dichloro-4-[(substituted sulfonyl)phenoxy]acetic acids of this invention have the following structural formula:

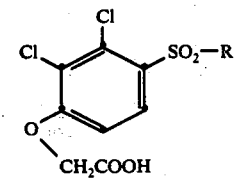

wherein R is

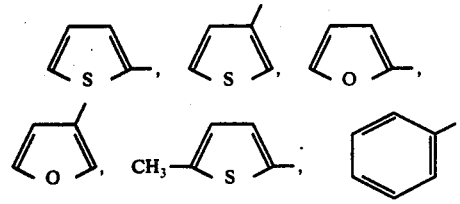

and the non-toxic pharmacologically acceptable salts, lower alkyl ester and amide derivatives thereof.

A preferred aspect of this invention are compounds of Formula I above wherein R is 2 or 3 thienyl and the non-toxic pharmacologically acceptable salt derivatives thereof.

The 2,3-dichloro-4-[(substituted sulfonyl)phenoxy]acetic acids can be prepared according to the following general equation.:

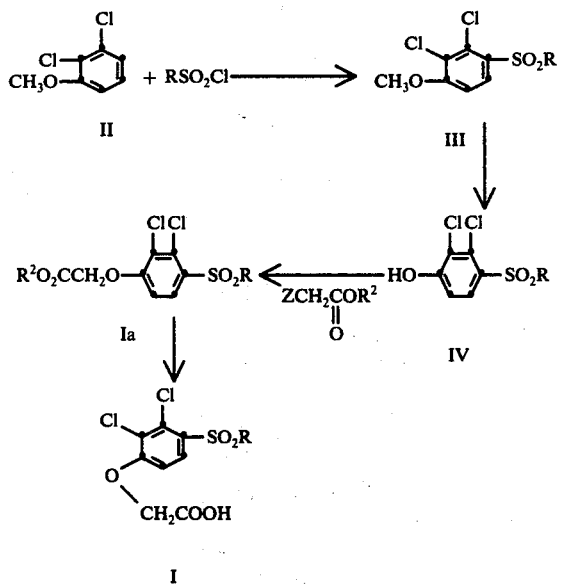

The first step of the reaction sequence involves reaction of 2,3-dichloroanisole with the substituted sulfonyl chloride in the presence of a Friedel-Crafts catalyst such as aluminum chloride and the like. The reaction solvent and the temperature at which this step is conducted are not particularly critical aspects of this reaction inasmuch as any solvent which is inert to the anisole (Compound I) and the substituted sulfonyl chloride may be employed with good results. In the instant regard the actual solvents can be the reactants themselves.

In order to convert the sulfonyl anisole drivative (III) to the sulfonylphenol (IV), one can treat the corresponding compound of Formula III with an ether cleaving reagent such as aluminum chloride, pyridine hydrochloride, sodium in liquid ammonia and the like. When aluminum chloride is employed the solvent may be heptane, carbon disulfide, methylene chloride and the like and when pyridine hydrochloride is employed it is not necessary to employ a solvent.

To convert the sulfonylphenol (compound IV) to the desired end products (I) one can use an etherification method which comprises reacting a halo acetic acid or ester thereof of the formula:

wherein $R^2$ is hydrogen or lower alkyl such as methyl or ethyl and Z is halo, such as bromo, chloro, or iodo with the sulfonylphenol compound (Formula IV). In general, this reaction is conducted in the presence of a base such as an akali metal carbonate, hydroxide or alkoxide such as potassium carbonate, sodium carbonate, potassium hydroxide, sodium hydroxide, sodium ethoxide and the like. Any solvent which is inert or substantially inert to the reactants and in which the reagents are reasonably soluble may be employed. Acetone, ethanol and dimethylformamide, for example, have proved to be particularly advantageous solvents. The reaction may be conducted at a temperature in the range of from about 25° C. to the reflux temperature of the particular solvent employed. The reaction with the haloacetic acid or ester is generally complete in about 10 to 60 minutes. If the haloacetic acid ester is employed, the ester obtained may be hydrolyzed to the free acid by methods well known to those skilled in the art.

As previously mentioned, the non-toxic, pharmacologically acceptable salts of the acids of Compound I are within the scope of this invention and are prepared by conventional methods well known in the art. Thus, the acid upon reaction with alkali metal and alkaline earth metal hydroxides, carbonates, bicarbonates, amines or quaternary ammonium hydroxides, forms the corresponding alkali metal, alkaline earth metal, amine or quaternary ammonium salt. These salts are particularly useful as parenteral solutions because they are very soluble in pharmaceutical carriers such as water or alcohol.

Also included within the scope of this invention are the ester and amide derivatives of the instant products which are prepared by conventional methods well known to those skilled in the art. Thus, for example, the ester derivative may be prepared by the reaction of an acetic acid compound of Formula I with an alcohol, for example with a lower alkanol. The amide derivatives may be prepared by converting an acid compound of Formula I its corresponding acid chloride by treatment with thionyl chloride followed by treating said acid chloride with ammonia, an appropriate mono-lower alkyl amine, di-lower alkyl amine or a hetero amine, such as piperidine or morpholine to produce the corresponding amide compound.

The following examples illustrate but do not limit the preparation of the various compositions of the invention.

EXAMPLE 1

Preparation of
[2,3-Dichloro-4-(2-thienylsulfonyl)phenoxy]-acetic acid

Step A: 2,3-Dichloro-4-(2-thienylsulfonyl)anisole

A stirred mixture of 2,3-dichloroanisole (4.5 g., 0.025 mole) and 2-thiophenesulfonyl chloride (4.6 g., 0.025 mole) is treated with aluminum chloride (3.5 g., 0.026 mole) over a 2 minute period. After 15 minutes, during which time the reaction solidifies, the reaction mixture is poured into warm water (150 ml.) containing hydrochloric acid (5 ml.). The 2,3-dichloro-4-(2-thienylsulfonyl)anisole which separates melts at 190° C. after recrystallization from benzene.

Elemental analysis for $C_{11}H_8Cl_2O_3S_2$: Calc.: C, 41.00; H, 2.50; Found: C, 40.73; H, 2.50.

Step B: 2,3-Dichloro-4-(2-thienylsulfonyl)phenol

A stirred mixture of 2,3-dichloro-4-(2-thienylsulfonyl)anisole (7.0 g.) and pyridine hydrochloride (70.0 g.) are heated in an oil bath at 185° C. for ½ hour and poured into water (300 ml.) to give 5.7 g. of 2,3-dichloro-4-(2-thienylsulfonyl)phenol which melts at 220° C. after recrystallization from ethanol.

Elemental analysis for $C_{10}H_6Cl_2O_3S_2$: Calc.: C, 38.84; H, 1.96; Found: C, 38.63; H, 2.02.

Step C: [2,3-Dichloro-4-(2-thienylsulfonyl)phenoxy]-acetic acid

A mixture of 2,3-dichloro-4-(2-thienylsulfonyl)phenol (5.3 g., 0.017 mole), potassium carbonate (4.8 g., 0.034 mole) and ethyl bromoacetate (5.7 g., 0.034 mole) in dimethylformamide (70 ml.) is heated at 55° C. in an inert atmosphere for ¾ hour then treated with 10N sodium hydroxide (5 ml.) in water (10 ml.) and heated at 95° C. for ¾ hour. The reaction solution is poured into dilute aqueous hydrochloric acid, extracted with ether, washed with water, dried over $MgSO_4$ and evaporated in vacuo to give 5.3 g. of [2,3-dichloro-4-(2-thienylsulfonyl)phenoxy]acetic acid. which melts at 179° C. after recrystallization from acetonitrile.

Elemental analysis for $C_{12}H_8Cl_2O_5S_2$: Calc.: C, 39.25; H, 2.20; Found: C, 39.11; H, 2.22.

EXAMPLE 2

By following substantially the procedure described in Example 1, Step A, but substituting for the 2-thiophenesulfonyl chloride therein described an equimolar amount of 3-thiophenesulfonyl chloride, 5-methyl-2-thiophenesulfonyl chloride, 2-furansulfonyl chloride, 3-furansulfonyl chloride or benzenesulfonyl chloride and conducting the procedures described in Example 1, Steps B and C, there is obtained: [2,3-Dichloro-4-(3-thienylsulfonyl)phenoxy]acetic acid;

[2,3-Dichloro-4-(5-methyl-2-thienylsulfonyl)phenoxy]acetic acid;

[2,3-Dichloro-4-(2-furansulfonyl)phenoxy]acetic acid;

[2,3-Dichloro-4-(3-furansulfonyl)phenoxy]acetic acid;

[2,3-Dichloro-4-benzenesulfonylphenoxy]acetic acid.

The compounds of this invention can be administered in a wide variety of therapeutic dosages in conventional vehicles as, for example, by oral administration in the form of a tablet or by intravenous injection. Also, the daily dosage of the products may be varied over a wide range as, for example, in the form of scored tablets containing 5, 10, 25, 50, 100, 150, 250 and 500 milligrams of the active ingredient for the symptomatic adjustment of the dosage to the patient to be treated. These dosages are well below the toxic or lethal dose of the products.

The following example is included to illustrate the preparation of a representative dosage form.

EXAMPLE 3

| Dry-filled capsules containing 50 mg. of active ingredient per capsule | |
|---|---|
| | Per Capsule |
| [2,3-Dichloro-4-(2-thienylsulfonyl)phenoxy]acetic acid | 50 mg. |
| Lactose | 149 mg. |
| Magnesium Stearate | 1 mg. |
| Capsule (Size No. 1) | 200 mg. |

The [2,3-dichloro-4-(2-thienylsulfonyl)phenoxy]acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

What is claimed is:

1. A compound of the formula:

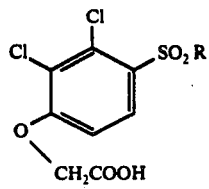

where R is

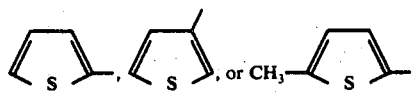

and the non-toxic pharmacologically acceptable acid addition salts, ester and amide derivatives thereof.

2. A compound of the formula:

wherein R is 2 or 3-thienyl and the non-toxic pharmacologically acceptable acid addition salts thereof.

3. A compound of claim 2 which is [2,3-dichloro-4-(2-thienylsulfonyl)phenoxy]acetic acid.

4. A compound of claim 2 which is [2,3-dichloro-4-(3-thienylsulfonyl)phenoxy]acetic acid.

* * * * *